(12) United States Patent
Won et al.

(10) Patent No.: US 8,486,905 B2
(45) Date of Patent: Jul. 16, 2013

(54) USE OF FLJ25416 GENE

(75) Inventors: Misun Won, Daejeon (KR);
Kyung-Sook Chung, Daejeon (KR);
Young-Joo Kim, Daejeon (KR);
Shin-Jung Choi, Daejeon (KR); Young Il Yeom, Daejeon (KR); Seon-Young Kim, Daejeon (KR); Kyung Bin Song, Daejeon (KR); Hee Gu Lee, Daejeon (KR); Eun Young Song, Seoul (KR); Young Ho Kim, Seoul (KR); Ho Kyung Chun, Seoul (KR); Chae-Ok Yun, Seoul (KR); Moon Hee Kim, Seoul (KR); Kyeong-Eun Jung, Anyang-si (KR); Sun-Jung Cho, Gyeongju-si (KR)

(73) Assignees: Korea Research Institute of Bioscience and Biotechnology, Daejeon (KR); St. Pharm Co., Ltd., Siheung-si (KR)

( * ) Notice: Subject to any disclaimer, the term of this patent is extended or adjusted under 35 U.S.C. 154(b) by 201 days.

(21) Appl. No.: 12/746,722

(22) PCT Filed: Dec. 5, 2008

(86) PCT No.: PCT/KR2008/007196
§ 371 (c)(1),
(2), (4) Date: Sep. 13, 2010

(87) PCT Pub. No.: WO2009/072831
PCT Pub. Date: Jun. 11, 2009

(65) Prior Publication Data
US 2011/0008370 A1    Jan. 13, 2011

(30) Foreign Application Priority Data

Dec. 6, 2007   (KR) .......................... 10-2007-0126222
Dec. 5, 2008   (KR) .......................... 10-2008-0122892

(51) Int. Cl.
*C12N 15/11*   (2006.01)
*C07H 21/02*   (2006.01)

(52) U.S. Cl.
USPC ......... 514/44 A; 536/23.1; 536/23.5; 530/350

(58) Field of Classification Search
USPC ....... 514/19.3, 44 A; 536/23.1, 23.5; 530/350
See application file for complete search history.

(56) References Cited

U.S. PATENT DOCUMENTS

| 6,852,318 B1 * | 2/2005 | Varner ........................ 424/130.1 |
| 2004/0197328 A1 * | 10/2004 | Young et al. ................ 424/141.1 |
| 2004/0258693 A1 * | 12/2004 | Young et al. ................ 424/155.1 |
| 2006/0183141 A1 | 8/2006 | Chang et al. |
| 2009/0162848 A1 * | 6/2009 | Nakaya et al. ..................... 435/6 |

FOREIGN PATENT DOCUMENTS

KR   10-2006-0031809 A   4/2006

OTHER PUBLICATIONS

Gura-antisense (Science, 1995, 270:575-577).*
Rihova (Advanced Drug Delivery Reviews, 1998, vol. 29, pp. 273-289).*
Gura (Science, 1997, 278:1041-1042).*
Snead et al. (Nucleic Acid Therapeutics, 2012, 22: 139-146).*
Juliano et al. (Mol Pharm. 2009, 6: 686-695).*
Taber's Cyclopedic Medical Dictionary (1985, F.A. Davis Company, Philadelphia, p. 274).*
Busken, C et al. (Digestive Disease Week Abstracts and Itinerary Planner, 2003, abstract No. 850).*
Kaiser (Science, 2006, 313: 1370).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Chang et al. (Oncol. Rep. Nov. 2009; 22(5):1119-27).*
N. Nakaya et al.: "Noxin, a novel stress-induced gene involved in cell cycle and apoptosis," Mol. Cell. Biol., vol. 27, No. 15, pp. 5430-5444, May 2007.

* cited by examiner

*Primary Examiner* — Stephen Rawlings
*Assistant Examiner* — Yan Xiao
(74) *Attorney, Agent, or Firm* — Rothwell, Figg, Ernst & Manbeck, P.C.

(57) ABSTRACT

Provided are a composition for diagnosing cancer or screening an anticancer drug comprising an FLJ25416 gene or an antibody directed to a protein expressed from the FLJ25416 gene, a composition for treating cancer comprising an inhibitor of the gene or an inhibitor of the protein expressed from the gene and a pharmaceutically acceptable carrier, and a kit for diagnosing cancer comprising at least one of the FLJ25416 gene and the protein expressed from the FLJ25416 gene. The FLJ25416 gene is expressed at high level in specific cancer cells, and induces an increase in proliferation rate of normal cells. The expression of the gene is suppressed, which results in an inhibitory effect on cancer cell growth. Thus, the FLJ25416 gene can be used as a target gene for diagnosis or treatment of cancer.

3 Claims, 6 Drawing Sheets

SEQUENCE LISTING

<160> NUMBER OF SEQ ID NOS: 11

<210> SEQ ID NO 1
<211> LENGTH: 3545
<212> TYPE: DNA
<213> ORGANISM: Homo sapiens

<400> SEQUENCE: 1

| | | | | | |
|---|---|---|---|---|---|
| gggagattcg | attggaaggc | tgccggcgtg | ctactgagtt | cggccggtcc | gagtcactgt | 60 |
| gcgtcgcctg | ggcgcgttcc | tggtcttctc | ccccagggtc | ttgctctgtc | acccaggctg | 120 |
| gagtgccatg | gcatcatcat | agctcactat | ggccttgatc | ctcctgcctt | agcctcccaa | 180 |
| gcagctggta | ttacagacca | cggtgtgaac | acatgaacag | aagacgaaaa | tttcttctag | 240 |
| cctcagtact | tgctctccag | aattcaagtt | ttatatatcc | atcatgtcag | aagtgcttct | 300 |
| ctaggataat | cctggtctcc | aaaaggtcta | attgtccaaa | atgtggctct | actggtgaat | 360 |
| ctggaaatgc | caattacaga | tacaaacttt | ccttaaaagt | tgcagaatca | aacaaattgt | 420 |
| ttgttattac | tgtatttgga | agttgcttag | atacattttt | tggtcttact | gccactggtt | 480 |
| tgcacaggta | cattcaggat | cctaataaaa | ttccagaaac | actggacaat | gatacaactc | 540 |
| agaatctatt | aactaaagca | gttgaaactt | gctttgttgg | acaaagcttt | attttggag | 600 |
| tgacgaattt | tgaaaaccaa | cctggacaag | gttcagatgc | cagtaacttc | ttacagcaat | 660 |
| gctctgacca | aaaagaaaa | gccaaagcac | tagtggcttg | ccagattgtt | ctaccagacc | 720 |
| caggtattgc | aggctttact | gtcattgact | acttccatca | acttttgcag | actttttaatt | 780 |
| tcaggaaact | tcagtgtgac | tctcaggcac | ctaacaatca | cttacttgct | ttagatcact | 840 |
| caaatagtga | tctcagcagc | acatatactt | ctgacagcac | ttctgatttt | ttcaagtcct | 900 |
| gcagcaagga | tactttttca | aaattctggc | agccatcact | tgaattcact | tgcattgttt | 960 |
| cacaactaac | agataatgat | gatttttcag | cttcagaaca | aagtaaggcc | tttggtactc | 1020 |
| ttcagcagaa | cagaaagtcc | atctccattg | cagaggccac | tggttccagt | agctgccatg | 1080 |
| atcccattca | ggattcatgg | agccttgttt | catatatgga | taaaaagagt | acagcagaaa | 1140 |
| agttgggtaa | agaacttggc | ttacaagcta | aggagctgag | tgcagttcac | agcagtcatc | 1200 |
| atgaaattgg | agttaatgac | tctaatttat | tctctttgga | aatgcgagag | ccccttgagt | 1260 |
| caagtaatac | aaaatccttc | cacagtgcag | tggaaattaa | aaataggtcc | cagcatgagc | 1320 |
| taccatgttt | tcagcatcat | ggtatagata | ccccaactag | ccttcagaag | agatctgcat | 1380 |
| gttgtccacc | ttcgttactc | agacttgaag | agacagccag | cagttcccag | gatggtgacc | 1440 |
| ctcaaatttg | ggatgatctg | ccattctctg | aaagcctgaa | caagtttctg | gcagttcttg | 1500 |
| aaagtgagat | tgctgtaacc | caggcagatg | tcagtagtag | gaaacatcat | gtagataatg | 1560 |
| acattgataa | atttcatgca | gaccacagca | gtttatctgt | gactccccag | agaactactg | 1620 |
| gagccctgca | tacaccacct | atagctttaa | gatcatcaca | agtaatagtc | aaagcaaact | 1680 |
| gtagcaaaga | tgacttcctt | ttcaactgta | aaggaaatct | aagtcctagt | gttgaaaagg | 1740 |
| agtcacaacc | agataacaaa | gtagaggctg | tctctgtaaa | tcataatgga | agagatatgt | 1800 |
| cagaatattt | tttaccgaat | ccttaccctgt | cagctctgtc | ttcatcttca | aaagatttag | 1860 |
| aaacaatagt | tactcttaag | aagactatca | gaatctcacc | acacagggag | agtgaccatt | 1920 |
| ctagtctaaa | taacaaatat | ttgaatggat | gtggagaaat | atcagtttca | gaaatgaatg | 1980 |
| aaaagttgac | aactctgtgt | tataggaagt | ataatgatgt | ctctgatctt | tgcaaattag | 2040 |

```
aaaataaaca atattgtagg tggtccaaga accaagatga cagttttaca atttgcagga    2100
aacttacata tcctttagaa actctttgca atagtccaaa tagaagtaca aatacattga    2160
aagaaatgcc ttggggacat atcaataaca acgtaacaca gagctattct attggttatg    2220
aaggtagcta tgatgcctct gctgatctct ttgatgtatat tgctaaagaa atggacattg    2280
caactgagat taccaaaaaa tcacaggata ttttgttaaa atggggaaca tctttggcag    2340
aaagtcaccc ttcagagtct gattttcac tgagatcact ttctgaagac ttcatccagc     2400
cttcacaaaa attatccttg caaagcctat ctgactctag gcattcaaga acatgctctc    2460
caacacctca ttttcaatca gattcagaat ataattttga aaatagtcaa gactttgttc    2520
catgttcaca gtcaactcca atttcagggt tccaccaaac aagaattcat gggataaaca    2580
gagctttcaa aaaacctgta ttttattcag atcttgatgg taactatgaa aaaataagga    2640
ttttccctga aaatgacaaa cagcaagcca gcccaagctg tccaaaaaat ataaaaacac    2700
ctagccagaa aatcagaagc cctattgtat ctggtatttc acaaccagac gttttcaatc    2760
actacccttt tgctgagtgc catgaaactg atagtgatga atgggtccct cctaccacac    2820
aaaaaatatt tccttcagat atgcttggat tccaaggcat aggtctaggg aaatgccttg    2880
ctgcctatca tttccctgat caacaagagt taccaagaaa gaaactgaaa catattagac    2940
aaggaaccaa taaggtttta attaagaaga aattaaagaa tatgcttgca gcagttgtta    3000
cgaaaaagaa aactcataaa tataactgta aaagttcagg ctggatttcc aaatgtccag    3060
acattcaagt cttagcagca cctcagctgc accctattct tggacctgat tcttgttcag    3120
aagtcaaatg ttgccttcca ttttcagaaa aaggcccacc ttcagtgtgt gaaactcgaa    3180
gtgcttggtc acctgaattg ttttcataaa aagtcacctg aacccaattc ctgaactttt    3240
aaatctgttt ggaaatgttt gccttcaggg gtacggaaag cattctttac attttgaaca    3300
cttggagaga agcaaattga aaacaggact ctgctgggag ctactgtgcc ttttaaaata    3360
taaagccatt gttttcccca gggttttatc tagaatacta tgattaggta gttgagcact    3420
ttatcttata ctgtttattg tactttaata atattgttaa gattgttttt gaaagtatta    3480
atgtttgtta aaatcacata tacatccaga aataaagact ttgcaaacca aaaaaaaaa    3540 aaaaa                                                                3545
```

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleuotide

<400> SEQUENCE: 2
cagaacagaa agtccatct                                                    19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleuotide

<400> SEQUENCE: 3
gatacaactc agaatctat                                                    19

<210> SEQ ID NO 4

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleuotide

<400> SEQUENCE: 4
gattcatgga gccttgttt                                                   19

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleuotide
<220> FEATURE:
<223> OTHER INFORMATION: Description of Combined DNA/RNA Molecule:
      Synthetic oligonucleuotide

<400> SEQUENCE: 5
cucgccggac acgcugaact t                                                21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cagaagccct attgtatctg g                                                21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtgaccaagc acttcgagtt t                                                21

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleuotide

<400> SEQUENCE: 8
ccuacgccac caauuucgu                                                   19

<210> SEQ ID NO 9
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleuotide

<400> SEQUENCE: 9
gatccccaga acagaaagtc catctttcaa gagaagatgg actttctgtt ctgttttttg      60
gaaa                                                                  64
```

```
<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
attgtcgaca atgaacagaa gacgaaaatt t                                   31

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccagatatct atgaaaacaa ttcaggtga                                      29
```

USE OF FLJ25416 GENE

CROSS REFERENCE TO RELATED APPLICATIONS

This application is a 35 U.S.C. §371 National Phase Entry Application from PCT/KR2008/007196, filed Dec. 5, 2008, and designating the United States, which claims priority under 35 U.S.C. §119 to Korean Patent Application No. 10-2007-0126222 filed Dec. 6, 2007 and to Korean Patent Application No. 10-2008-0122892 filed Dec. 5, 2008, which are incorporated herein in their entireties.

TECHNICAL FIELD

The present invention relates to a composition for cancer diagnosis or anticancer drug screening, comprising an FLJ25416 gene or a protein expressed from the FLJ25416 gene, a composition for treatment of cancer, comprising an inhibitor of the gene or an inhibitor of the protein and a pharmaceutically acceptable carrier, a cancer diagnosis kit comprising at least one of an FLJ25416 gene and a protein expressed from the FLJ25416 gene, a method for diagnosing cancer, a method for treating cancer, and a method for screening anticancer drugs.

BACKGROUND ART

The completion of the Human Genome Project, which allows understanding of human diseases at the molecular level, identification of target molecules for diseases and further understanding of molecular mechanism of diseases, has opened an era of post-genomics. The information and insights obtained from human genomics are leading to technology for development of personalized medicine for human diseases. With personalized medicine, patients can be treated by selecting the appropriate drugs. Also, pharmacogenomic technology involving identification of biomarkers, targeted therapy, disease-specific mode of action of drugs, clinical and genomic information of patients, genome epidemic, and bioinformatic analysis should be complementarily integrated. In particular, technology involving prediction of the drug action in each individual, identification of diagnostic biomarkers, identification of novel target genes and proteins, and development of therapeutic agents are crucial for competitiveness in personalized medicine.

Recently, there has been fierce competition all over the world to identify therapeutic targets through research into the functions of genes related to generation and treatment of a serious disease such as cancer. The therapeutic targets can be used to diagnose cancer and develop new therapeutic agents. Along with such active genomic research, human genomic DNA chip or proteomic analysis has also been progressing, resulting in the finding of a large number of genes related to cancer and the accumulation of a database cataloging the various genes. However, since the particular biological functions in cells and relevance to cancer of most genes have not been fully discovered, in reality, the genes are still difficult to be used to confirm its relevance to cancer or used as diagnostic or target genes for cancer diagnosis.

Meanwhile, in response to increasing demand for research on the functions of various human genes, more attention is turning to a model organism for simple functional and morphological research. In order to understand evolutionarily well-preserved mechanisms fundamentally occurring in cells, there has been process in studying the application of model organisms, which have long had various applications, to diagnose cancer or identify therapeutic targets.

RNA interference (RNAi) is a powerful tool for clearly identifying genes that are overly expressed in cancer cells as possible targets for treating cancer. RNAi triggers sequence-specific degradation of mRNA homologous with a base sequence of interest in cells using various forms of oligo double-stranded RNAs (oiligo dsRNAs), such as microRNAs (miRNAs), expressed dsRNAs and synthetic small interference RNAs (siRNAs), such that the function of the gene is suppressed. Target validation as a cancer target is carried out by examining phenotypical changes of the cells inhibited in gene expression to identify the function of the corresponding gene and signal transmission pathways, which is used to develop novel drugs.

Among the oligo dsRNAs capable of being used for RNAi, a siRNA-mediated technique (pathway) has drawn attention in recent times for being a phenomenal tool, and was even named the "breakthrough of the year" by the Journal of Science (2002). siRNA is a short dsRNA having 19 to 23 bps. Once introduced into a cell, it exhibits a specific inhibition effect on a specific gene. siRNA that is complementary to a gene activating generation of cancer and inhibiting apoptosis would inhibit the function of the gene in cells, thereby killing cancer cells and validating a target gene for treating cancer. Thus, siRNA study has been actively conducted for identification of a disease-specific target gene, target gene validation, and therapeutic agent development.

Meanwhile, the FLJ25416 genes (GenBank Accession NOs: FLJ25416 and FLJ13936, UniProtKB/TrEMBL entry Q8IXT1) are genes for hypothetical proteins whose functions are not yet known.

DISCLOSURE OF THE INVENTION

Technical Problem

Therefore, the present invention has been made in view of the above problems, and it is an object of the present invention to provide a novel use of an FLJ25416 gene.

More specifically, an object of the present invention is to provide a composition for diagnosing cancer or for screening anticancer drugs comprising an FLJ25416 gene or an antibody to a protein expressed from the FLJ25416 gene; a composition for preventing or treating cancer comprising an inhibitor of the aforesaid gene or an inhibitor of the aforesaid protein and a pharmaceutically acceptable carrier; and a kit for diagnosing cancer comprising one or more selected from an FLJ25416 gene and a protein expressed from the FLJ25416 gene.

It is another object of the present invention to provide a method for diagnosing and treating cancer, and a method for screening an anticancer drug.

Technical Solution

In accordance with an aspect of the present invention, the above and other objects can be accomplished by the provision of a composition for diagnosing cancer, comprising an FLJ25416 gene.

As used herein, the term "FLJ25416 gene" refers to a full-length DNA or RNA of the FLJ25416 gene, or a portion or variant thereof.

In addition to the genes, the composition of the present invention may further comprise buffer or distilled water to stably maintain a structure of nucleic acid.

As can be confirmed from Examples 1 through 4 which will be illustrated hereinafter, the expression level of an FLJ25416 gene is specifically increased in cancer cells or cancer cell lines. Thus, the diagnosis of cancer can be performed by analysis of the overexpression of the FLJ25416 gene.

In accordance with another aspect of the present invention, there is provided a use of an FLJ25416 gene for manufacturing a formulation for diagnosing cancer, and a method for diagnosing cancer, comprising confirming the reaction between a sample obtained from a subject and the FLJ25416 gene.

In the method for diagnosing cancer according to the present invention, for confirming the reaction between a sample obtained from a subject and an FLJ25416 gene, it is possible to use any conventional methods used in the in vivo and in vitro cases of DNA-DNA, DNA-RNA or DNA-protein, for example, DNA chip, protein chip, polymerase chain reaction (PCR), Northern blotting, Southern blotting, enzyme linked immunosorbent assay (ELISA), yeast two-hybrid assay, 2-D gel electrophoresis, in vitro, binding assay, etc. For example, incidence of cancer (carcinogenesis) in individuals can be determined by examining whether a gene of interest is expressed at a high level in a subject, through hybridization of an intact or partial gene as a probe with the nucleic acid isolated from a body fluid of the subject, and detection of a hybridization product according to any conventional method known in the art, such as reverse transcription-polymerase chain reaction (RT-PCR), Southern blotting, Northern blotting, and the like. When the probe is labeled with a suitable label material such as radioisotopes, enzymes, and the like, it is possible to readily confirm the presence of the target gene.

In accordance with a further aspect of the present invention, there is provided a composition for diagnosing cancer, comprising a protein expressed from an FLJ25416 gene.

In addition to the aforesaid protein, the composition of the present invention may further comprise buffer or distilled water to stably maintain a structure of the protein.

As discussed above, the expression level of the FLJ25416 gene is specifically increased in cancer cells. Therefore, the presence of cancer can be diagnosed by analysis of the overexpression of the FLJ25416 gene or the corresponding protein, using the protein expressed from the FLJ25416 gene.

In accordance with a still further aspect of the present invention, there is provided a use of the aforesaid protein for manufacturing a formulation for diagnosing cancer, and a method for diagnosing cancer, comprising confirming the reaction between the protein expressed from the FLJ35426 gene and a sample obtained from a subject.

In the cancer diagnosis method according to the present invention, for confirming the reaction between the subject-derived sample and the protein, it is possible to use any conventional methods used in the in vivo and in vitro cases of DNA-protein, RNA-protein or protein-protein, for example, DNA chip, protein chip, PCR, Northern blotting, Southern blotting, Western blotting, ELISA, histoimmunostaining, yeast two-hybrid assay, 2-D gel electrophoresis, in vitro binding assay, etc. For example, incidence of cancer (carcinogenesis) in individuals can be determined by examining whether a gene of interest is expressed at a high level in a subject, through hybridization of an intact or partial protein as a probe with the nucleic acid isolated from a body fluid of the subject, and detection of a hybridization product according to any conventional method known in the art, such as RT-PCR, Western blotting, and the like. When the probe is labeled with a suitable label material such as radioisotopes, enzymes, and the like, it is possible to readily confirm the presence of the target gene.

Alternatively, the composition of the present invention may comprise an antibody specific for the protein, instead of the protein. As an FLJ25416 gene is overexpressed in cancer cells, the expression level of the protein expressed from the gene is also increased. Therefore, when an antibody directed against the protein expressed from the gene is used, it is possible to diagnose cancer by detecting the protein through an antigen-antibody reaction.

Monoclonal antibodies directed against the aforesaid protein may be produced by any conventional method for production of monoclonal antibodies known in the art or otherwise may be commercially available. Quantitative analysis of monoclonal antibodies against the aforesaid proteins may be generally carried out by color development using secondary antibodies conjugated with a certain enzyme (such as alkaline phosphatase (AP) or horseradish peroxidase (HRP)) and substrates thereof, or otherwise may be carried out using the protein-specific monoclonal antibodies which are directly conjugated with AP or HRP enzymes. Alternatively, instead of monoclonal antibodies, it may also be possible to use polyclonal antibodies which recognize the aforesaid protein. These polyclonal antibodies may be obtained by any conventional method for production of antiserum known in the art.

Further, the present invention provides a use of the antibody specific for the aforesaid protein for manufacturing a formulation for diagnosing cancer, and a method for diagnosing cancer, comprising confirming the reaction between the antibody specific for the aforesaid protein and a subject-derived sample.

Further, the present invention provides a composition for screening anticancer drugs, comprising an FLJ25416 gene. Further, the present invention provides a use of an FLJ25416 gene for manufacturing a formulation for screening anticancer drugs, and a method for screening anticancer drugs, comprising contacting a test material with the gene as a target material, and confirming the reaction between the target material and the test material to determine whether the test material activates or suppresses the expression of the FLJ25416 gene.

In the screening method according to the present invention, the reaction between the target material and the test material can be confirmed by any conventional method used in the in vivo and in vitro cases of DNA-DNA, DNA-RNA, DNA-protein, or DNA-compound. For example, mention may be made of a hybridization test to confirm binding of the gene to the test material in vitro, a method of determining a gene expression level involving reacting of mammalian cells with the test material, and subjecting the reaction product to Northern blot analysis, quantitative PCR, or quantitative real-time PCR, and a method of determining an expression level of a reporter gene involving linking the reporter gene to the gene of interest, introducing the resulting gene construct into a cell and reacting the cell with a test material. In this case, the composition of the present invention may further comprise distilled water or buffer to stably maintain a structure of the nucleic acid, in addition to the aforesaid gene.

Further, the present invention provides a composition for screening anticancer drugs, comprising a protein expressed from an FLJ25416 gene. Further, the present invention provides a use of the protein for manufacturing a formulation for screening anticancer drugs, and a method for screening anticancer drugs, comprising a test material with the aforesaid protein as a target material, and confirming the reaction between the target material and the test material to determine whether the test material activates or suppresses the function of the protein.

The anticancer drug may be a low-molecular weight compound or a natural product.

In the screening method according to the present invention, the reaction between the protein and the test material can be confirmed by any conventional method used in the cases of protein-protein, DNA-compound and the like. For example, mention may be made of a method of determining activity of a test material after reaction of the protein with the test material, yeast two-hybrid assay, detection of phage-displayed peptide clones bound to the aforesaid protein, high throughput screening (HTS) using natural products and chemical libraries, drug hit HTS, cell-based screening, and DNA array screening. In addition to the protein component, the composition of the present invention may further comprise buffer or reaction liquid to stably maintain a structure or physiological activity of the corresponding protein. For in vivo experiments, the composition of the present invention may comprise cells expressing the aforesaid protein, or cells harboring a plasmid that expresses the aforesaid protein under a promoter capable of controlling a transcription rate.

In the screening method of the present invention, the test material may be a material which is suspected to have the possibility of being an anticancer drug according to conventional criteria and a strategy for selection, or may be a material which is randomly selected, such as individual nucleic acids, proteins, extracts or natural products, low-molecular weight compounds, and the like.

There may be two types of test materials which are obtained through the screening method of the present invention: a material capable of enhancing the gene expression or protein function and a material capable of inhibiting the gene expression or protein function. The former material may become an anticancer drug candidate via development of an inhibitor against the test material, whereas the latter material may serve directly as an anticancer drug candidate. These anticancer drug candidates will serve as a leading compound during a subsequent development process of anticancer drugs. A novel anticancer drug can be created by structural modification and optimization of the leading compound such that the leading compound can exhibit inhibitory effects on function of the gene or expression products thereof.

Further, the present invention provides a composition for treating cancer, comprising an inhibitor of an FLJ25416 gene. The composition may further comprise one or more pharmaceutically acceptable carriers.

As can be confirmed from Examples which will be illustrated hereinafter, the gene of the present invention is expressed at a high level in cancer cells, and administration of an inhibitor against the aforementioned gene (hereinafter, referred to as "gene inhibitor") can suppress the gene expression to thereby inhibit incidence of cancer.

Therefore, the present invention provides a use of a gene inhibitor for manufacturing a formulation for treating cancer, and a method for treating cancer, comprising administering a therapeutically effective amount of the gene inhibitor to a subject in need thereof. As used herein, the terms "treating cancer," "treatment of cancer" and "cancer treatment" encompass prevention and inhibition of cancer.

In the present invention, the gene inhibitor may be an antisense oligonucleotide for mRNA of the FLJ25416 gene.

The antisense oligonucleotide has been successfully employed to achieve gene-specific inhibition both in vivo and in vitro. The antisense oligonucleotide is a short synthetic DNA strand (or DNA analog) which is antisense (or complementary) to a certain DNA or RNA target. The antisense oligonucleotide is proposed to prevent expression of the protein encoded by a DNA or RNA target. For this purpose, the antisense oligonucleotide binds to the target to thereby halt the protein expression at a transcription, translation or splicing stage. Further, the antisense oligonucleotide has been successfully used in cell culture and animal models of disease (Hogrefe, 1999). Additional modification of antisense oligonucleotides to ensure that oligonucleotide is more stable and resistant against in vivo nuclease degradation may be carried out by any conventional method well known to those skilled in the art. As used herein, the term "antisense oligonucleotide" encompasses double-stranded DNAs (dsDNAs) or single-stranded DNAs (ssDNAs), dsRNAs or ssRNAs, DNA/RNA hybrids, DNA and RNA analogs, and oligonucleotides having modifications of base, sugar, and/or backbone. The oligonucleotide may be chemically modified to improve the stability thereof and increase the resistance against nuclease degradation, according to a conventional method known in the art. These modification methods are conventionally known in the art, and may include, but are not limited to, modifications of the oligonucleotide backbone, sugar moieties and bases.

Further, the gene inhibitor may be small interfering RNA (siRNA) of the FLJ25416 gene.

siRNA even at a relatively low concentration can achieve inhibitory effects on gene expression comparable to or higher than those obtained by the antisense oligonucleotide and therefore is proposed as a substitute for the antisense oligonucleotide (Thompson, 2002). siRNAs are widely utilized for inhibition of gene expression in animal models of disease. siRNA has a promising potential as a very strong inhibitor drug on in vivo expression of a certain gene, in view of the long retention time upon cell culture and under in vivo conditions, in vivo transfection capacity and resistance against serum degradation (Bertrand et al., 2002). Expression constructs/vectors comprising siRNA and transfection effects of siRNA are known to those skilled in the art. For example, US Patent Publication Nos. 20040106567 A1 and 20040086884 A1 disclose a variety of delivery mechanisms, such as viral and non-viral vectors comprising siRNA, liposome delivery systems, in vivo injection systems of plasmid DNAs, artificial viral envelope and polylysine conjugates, and information of the expression constructs/vectors.

Those skilled in the art will appreciate that it is possible to synthesize and modify the antisense oligonucleotide and siRNA as desired, using any conventional method known in the art (see Andreas Henschel, Frank Buchholz and Bianca Habermann (2004) DEQOR: a web-based tool for the design and quality control of siRNAs. Nucleic Acids Research 32 (Web Server Issue):W113-W120).

Further, the gene inhibitor may be short hairpin RNA (shRNA) of the FLJ25416 gene. The shRNA is a single-strand consisting of 45 to 70 nucleotides. An oligo DNA having sense sequence and its complimentary nonsense sequence of target gene siRNA linked via a linker having 3 to 10 bases is synthesized. Then, the resulting oligo DNA is cloned into a plasmid vector or lentivirus, which is retrovirus, or adenovirus to express, thereby forming a loop sequence of the shRNA. The resulting sequence is cleaved by Dicer in the viral cell to generate siRNA, which will exhibit RNAi effects. shRNA exhibits RNAi effects for a relatively long time, as compared to siRNA.

Expression constructs/vectors comprising shRNA are known to those skilled in the art. For example, US Patent Publication Nos. 20040106567 A1 and 20040086884 A1 disclose information about a variety of expression constructs/vectors, such as viral vectors comprising shRNA.

Further, it will be apparent to those skilled in the art that there are a variety of regulatory sequences (for example, constitutive or inducible promoters, tissue-specific promoters, a combination thereof, etc.) which are useful for the antisense oligonucleotide, siRNA, or shRNA expression construct/vector.

The antisense oligonucleotide, siRNA, or shRNA of the present invention, which is used for treatment of cancer, may be administered in the form of a composition further comprising pharmaceutically acceptable carrier(s). Examples of suitable pharmaceutically acceptable carriers may include water, saline, PBS (phosphate buffered saline), dextrin, glycerol, ethanol and a combination thereof. Additionally, the composition of the present invention may be appropriately formulated by a conventional method known in the art, such that it is possible to achieve fast, sustained or delayed release of active ingredients after administration of the composition.

The gene inhibitor may be antisense oligonucleotides, siRNAs, or shRNAs, as well as any material capable of inhibiting expression of a gene of interest. Therefore, it is possible to use compounds known as the inhibitor of the aforementioned gene in the art.

Further, the present invention provides a composition for treating cancer, comprising an inhibitor of the protein expressed from the FLJ25416 gene (hereinafter, referred to as "protein inhibitor"). The composition may further comprise one or more pharmaceutically acceptable carriers.

Suppression of the gene of the present invention results in subsequent inhibition of the corresponding protein expression to thereby inhibit development and/or progress of cancer. Consequently, it is possible to inhibit development of cancer via suppression of expression of the corresponding protein from the FLJ25416 gene.

Therefore, the present invention provides a use of a protein inhibitor for manufacturing a formulation for treating cancer, and a method for treating cancer, comprising administering a therapeutically effective amount of the same protein inhibitor to a subject in need thereof. As used herein, the terms "treating cancer," "treatment of cancer" and "cancer treatment" encompass prevention and inhibition of cancer.

The protein inhibitor may be nucleic acids, compounds, natural products, low-molecular weight compounds or proteins. For example, the protein inhibitor may be an antibody directed against the protein expressed from the gene of the present invention. Monoclonal antibodies directed against the aforesaid protein may be produced by any conventional method for production of monoclonal antibodies known in the art or otherwise may be commercially available. Alternatively, instead of monoclonal antibodies, it may also be possible to use polyclonal antibodies which recognize the aforesaid protein. These polyclonal antibodies may be obtained by any conventional method for production of antiserum known in the art.

For purpose of desired administration, the composition of the present invention may be formulated into a variety of dosage forms by further inclusion of one or more pharmaceutically acceptable carriers in combination with the above-mentioned active ingredient. When the inhibitor against the protein of the present invention is an antibody, the pharmaceutically acceptable carrier may be comprised of a minimum amount of an additive to improve a shelf life or effectiveness of a binding protein, such as a wetting agent, emulsifier, preservative or buffer.

Further, the anticancer composition of the present invention may be used in combination with one or more anticancer drugs. The anticancer composition may further comprise chemotherapeutic agents well-known to those skilled in the art, for example, alkylating agents such as cyclophosphamide, aziridine, alkyl alkone sulfonate, nitrosourea, dacarbazine, carboplatin, cisplatin, and the like, antibiotics such as mitomycin C, anthracycline, doxorubicin (Adriamycin), and the like, antimetabolic agents such as methotrexate, 5-fluorouracil (5-FU) and cytarabine, plant-derived agents such as Vinca alkaloids, and hormones.

The composition of the present invention may further comprise pharmaceutically and physiologically acceptable additives, in addition to the active ingredient. Examples of such additives may include excipients, disintegrating agents, sweeteners, binders, coating agents, blowing agents, lubricants, glidants, solubilizers, etc.

For administration, the composition of the present invention may further comprise one or more pharmaceutically acceptable carriers, in addition to the active ingredient, to be formulated to a pharmaceutical composition appropriately.

For formulation of the composition into a liquid preparation, a pharmaceutically acceptable carrier which is sterile and biocompatible may be used such as saline, sterile water, Ringer's solution, buffered physiological saline, albumin infusion solution, dextrose solution, maltodextrin solution, glycerol, and ethanol. These materials may be used alone or in any combination thereof. If necessary, other conventional additives may be added such as antioxidants, buffers, bacteriostatic agents, and the like. Further, diluents, dispersants, surfactants, binders and lubricants may be additionally added to the composition to prepare injectable formulations such as aqueous solutions, suspensions, and emulsions, or oral formulations such as pills, capsules, granules, and tablets. Furthermore, the composition may be preferably formulated into a desired dosage form, depending upon diseases to be treated and ingredients, using any appropriate method known in the art, as disclosed in "Remington's Pharmaceutical Sciences," Mack Publishing Co., Easton, Pa.

Dosage forms of the composition of the present invention may include granules, powders, coated tablets, tablets, capsules, suppositories, syrups, juices, suspensions, emulsions, drops or injectable liquid formulations and sustained-release formulations of active ingredient(s).

The pharmaceutical composition can be administered via a conventional route, for example, intravenously, intraarterially, intraperitoneally, intramuscularly, intrathoracically, percutaneously, intranasally, locally, rectally, orally, intraocularly, intradermally, or by inhalation.

As used herein, the term "therapeutically effective amount" refers to an amount of an active ingredient that is required to exert anticancer effects. As will be apparent to those skilled in the art, the effective dose of the active ingredient in accordance with the present invention may vary depending upon various factors such as kinds of disease, severity of disease, kinds and contents of active ingredients and other components contained in the composition, kinds of dosage forms, age, weight, health, sex and dietary habits of patients, administration times and routes, release rates of the composition, treatment duration, and co-administered drugs. For adults, when the gene or protein inhibitor is administrated one or more times a day, the dosages are preferably in ranges of 0.01 ng/kg to 30 mg/kg for shRNA, 0.01 ng/kg to 10 mg/kg for siRNA, 0.01 ng/kg to 10 mg/kg for antisense oligonucleotide to mRNA of the aforesaid gene, 0.1 ng/kg to 10 mg/kg for a compound, and 0.1 ng/kg to 10 mg/kg for a monoclonal antibody directed against the aforesaid protein, respectively.

Further, the present invention provides a kit for cancer diagnosis, comprising at least one of an FLJ25416 gene, and a protein expressed from the FLJ25416 gene.

In addition to the diagnostic composition of the present invention, the cancer diagnosis kit may further comprise a material for application of DNA chips, protein chips, etc., which are used to examine the reaction of the composition with a test sample.

In one embodiment of the present invention, the FLJ25416 gene may have a nucleotide sequence of SEQ ID NO: 1 or its variant sequence with deletion, substitution or insertion of one or more bases.

In another embodiment of the present invention, the FLJ25416 siRNA may have a nucleotide sequence among one or more sense sequences selected from SEQ ID NOs: 2, 3 and 4.

In the other embodiment of the present invention, the FLJ25416 shRNA may have a nucleotide sequence coded by a DNA sequence of SEQ ID NO: 9.

Further, it will be apparent to those skilled in the art that the aforementioned sequences of FLJ25416 gene, and siRNA or shRNA of the FLJ25416 gene are provided for illustration only and are not necessarily representative of the sequences for the purpose of limiting the invention. Sequences having substantial sequence identity or homology to the above-mentioned sequences also fall within the scope of the present invention. As used herein, the term "substantial sequence identity" or "substantial sequence homology" is used to indicate that a sequence of interest exhibits substantial structural or functional equivalence with another sequence. Differences may be due to inherent variations in codon usage among different species, for example. Structural differences are considered de minimis if there is a significant amount of sequence overlap or similarity between two or more different sequences or if the different sequences exhibit similar physical characteristics even if the sequences differ in length or structure.

In the present invention, cancers to be treated include lung cancer, non small cell lung cancer, osteosarcoma, pancreas cancer, skin cancer, head or neck cancer, melanoma of skin or eye, uterine cancer, ovarian cancer, rectal cancer, gastric cancer, anal cancer, colon cancer, breast cancer, fallopian tube cancer, endometrial cancer, cervical cancer, vaginal cancer, vulvar cancer, Hodgkin's disease, esophageal cancer, small intestine cancer, endocrine gland cancer, thyroid cancer, parathyroid cancer, adrenal cancer, soft tissue sarcoma, urethral cancer, penis cancer, prostatic carcinoma, acute or chronic leukemia, lymphoma, bladder cancer, kidney or ureteral cancer, renal cell carcinoma, renal pelvis carcinoma, central nervous system (CNS) carcinoma, primary CNS lymphoma, spinal tumor, brain stem glioma and pituitary adenoma.

The matters relating to genetic engineering technologies will be more explicit from the written text described in Sambrook et al., Molecular Cloning, A Laboratory Manual, Cold Spring Harbor Laboratory Press, Cold Spring Harbor, N.Y. (2001) and Frederick M. Ausubel et al., Current Protocols In Molecular Biology, volume 1, 2, 3, John Wiley & Sons, Inc. (1994).

Advantageous Effects

A composition according to the present invention is effective in diagnosis of cancer, screening of an anticancer drug and cancer treatment. As a result, it is expected that the present invention will be used for research and development of personalized anticancer drugs having low adverse side effects. Further, the present invention will contribute to the development of source technology which forms the basis of study of new cancer-related mechanisms.

MODE FOR INVENTION

The present invention will be described in more detail with reference to the following Examples.

These and other objects, advantages and features of the present invention will become apparent from the detailed embodiments given below which are made in conjunction with the following Examples. The present invention may be embodied in different forms and should not be misconstrued as being limited to the embodiments set forth herein, and those skilled in the art will appreciate that various modifications, additions and substitutions are possible without departing from the scope and spirit of the invention as disclosed in the accompanying claims. Therefore, it should be understood that the embodiments disclosed herein are provided only for illustrating the present invention and should not be construed as limiting the scope and spirit of the present invention.

EXAMPLE 1

Overexpression of FLJ25416 Gene in Cancer Cell Lines

The simple validation of a gene for relevance to cancer is to compare expression levels of a gene of interest in cancer tissues or cancer cell lines. The validation of the gene for relevance to cancer according to the expression level is carried out by examining the increase or decrease in expression level according to generation and proliferation of cancer, compared to normal cells. To this end, RT-PCR was performed using total RNAs obtained from cancer cell lines and oligonucleotide of the gene of interest to examine expression levels of the gene in cancer cell lines, compared to normal cells.

Therefore, in the present invention, expression levels of the FLJ25416 gene in human gastric and liver cancer cell lines, and normal cells were analyzed by RT-PCR. The gastric cancer cell lines used are Snu620, Snu216, Snu484, Snu601 and Snu638 (Korean Cell Line Bank, Seoul National University, Korea). The liver cancer cell lines used are Huh7, SH-J1, and Ck-1a (courtesy of Dr. Dae Ghon Kim, Chonnam National University, Korea), Chang (ATCC #CCL13), Snu709 and Snu354 (Korean Cell Line Bank, Seoul National University, Korea). In addition, as a normal cell control, IMR90 (human fetal lung fibroblasts, ATCC #CCL-186) was used. Total RNA was purified using the Qiagen RNeasy Mini kit. RT-PCR was carried out using the One-step RT-PCR PreMix kit (iNtRON Biotechnology, Inc., Korea). The kit is manufactured for one time synthesis and amplification of cDNA. RT-PCR was carried out by forming a total 20 µl of cocktail consisting of an RNA template (1 µg/reaction) obtained from each cancer cell, specific primers, tertiary distilled water and 8 µl of PreMix (OptiScript™ RT and i-StarTaqTMDNA polymerase). The specific primers used for RT-PCR are listed in Table 1.

TABLE 1

| | N-terminal primer | C-terminal primer |
|---|---|---|
| FLJ25416 | SEQ ID NO: 6<br>5'-CAGAAGCCCTATT<br>GTATCTGG-3' | SEQ ID NO: 7<br>5'-GTGACCAAGCACTT<br>CGAGTTT-3' |

Figure 1:
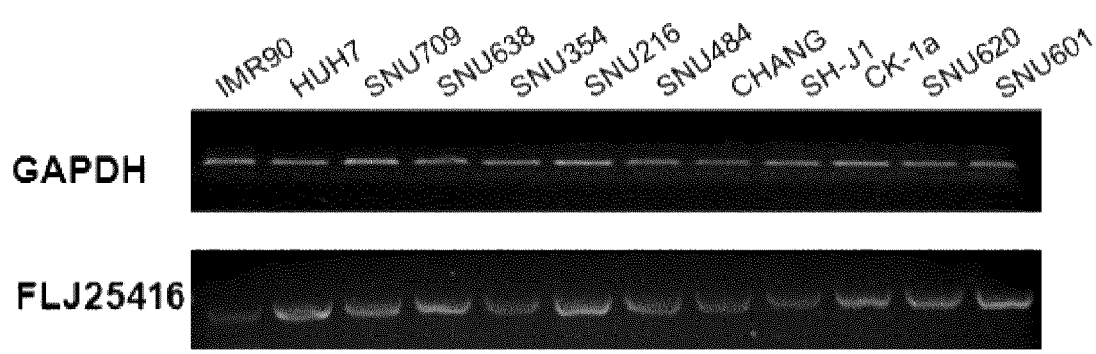
FIG. 1 illustrates comparison of expression levels of an FLJ25416 gene in human gastric and liver cancer cell lines, and normal cells, using RT-PCR, wherein GAPDH is a control.

From the RT-PCR result, it can be confirmed that the mRNA expression levels of the FLJ25416 gene were significantly increased in various cancer cell lines, compared to the normal cell line (FIG. 1). In FIG. 1, glyceraldehydre-3-phosphate dehydrogenase (GAPDH) was used as a control for comparison.

This result reveals that the increase in expression levels of the FLJ25416 gene can be used as a diagnostic index for cancer.

EXAMPLE 2

Microarray Analysis for Examining Overexpression of FLJ25416 Gene in Tissues of Colon Cancer Patients Colon cancer tissues from 66 patients and normal tissues were obtained at Samsung Medical Center (Seoul, Korea). Tissues were surgically removed from respective patients, and then stored in liquid nitrogen until analysis.

Total RNA was purified using the QIAGEN kit (RNeasy Maxi kit: cat #75162), and quantitated using the Experion RNA StdSens chip (Bio-Rad Laboratories). First, clinical tissues of colon cancer and normal tissues were cut into appropriate sizes, and then lysed in 15 ml of lysis buffer included in the kit to which 1500 of beta mercaptoethanol was added. Here, 15 ml of 70% ethanol was well mixed with the lysate, which was centrifuged at 3000×g for 5 minutes, resulting in attaching the total RNA to a membrane. The resulting membrane was washed twice, and 1.2 ml of RNase-free water was then added to thereby isolate the total RNA. Attached cell lines were recovered using trypsin and EDTA, and then lysed in 1 ml of lysis buffer included in the kit.

The extracted total RNA was hybridized using the Illumina TotalPrep RNA Amplification Kit (Ambion). cDNA was synthesized using a T7 Oligo (dT) primer, and then biotin-labeled cRNA was generated using a biotin-UTP in a process of in vitro transcription. The generated cRNA was quantitated using NanoDrop. The cRNAs prepared from normal colon epithelial cells and colon cancer cells were hybridized to Human-6 V2 chips (Illumina). After hybridization, to remove non-specific hybridization, the DNA chips were washed with Illumina Gene Expression System washing solution (Illumina), and then labeled with streptavidin-Cy3 (Amersham), which is a fluorescence dye. The fluorescence-labeled DNA chips were scanned using a confocal laser scanner (Illumina) to obtain fluorescence data present in respective spots, and the scanned data were saved in TIFF image files. The TIFF image files were processed by BeadStudio version 3 software (Illumina) to analyze fluorescent levels of the respective spots. The analyzed result was normalized by the 'quantile' function of the Avadis Prophetic version 3.3 software (Strand Genomics).

Figure 2:
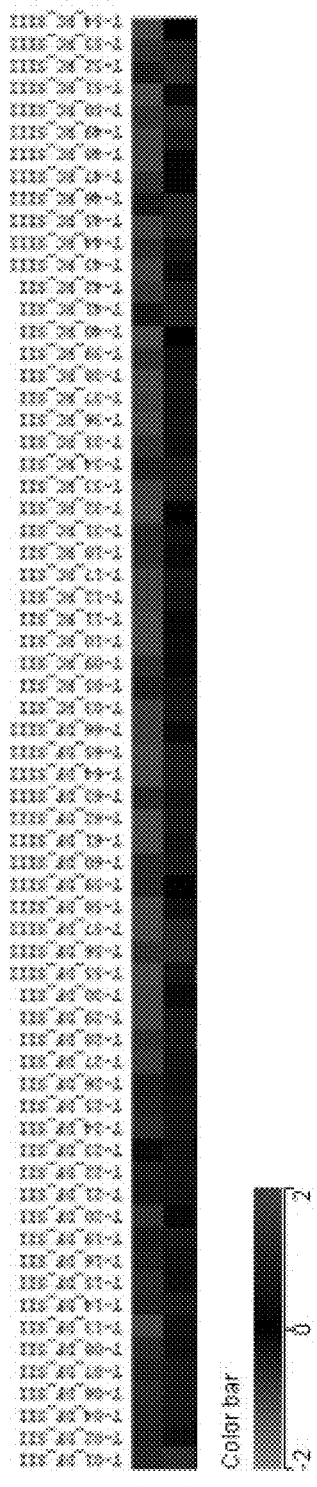
FIG. 2 illustrates the results for microarray assay using Illumina 48K chip, which show an increase in expression levels of FLJ25416 gene in tissues obtained from a colon cancer patient.

The result is shown in FIG. 2, which illustrates FLJ25416 gene expression profiles assessed in cancer tissues of colon cancer patients and normal tissues. Here, up-regulating genes and down-regulating genes are shown in red and green, respectively. In FIG. 2, *Homo sapiens* actin, beta (ACTB) was used as a control in order to determine a difference in gene expression. The FLJ254156 gene was up-regulated about 5-fold in cancer tissues.

This result reveals that the increase in expression levels of the FLJ25416 gene can be used as a diagnostic index for cancer.

EXAMPLE 3

Expression Analysis for FLJ25416 Gene in Colon Cancer Tissues by RT-PCR

The simple validation of a gene for relevance to cancer is to compare expression levels of a gene of interest in cancer tissues or cancer cell lines. The validation of the gene for relevance to cancer according to the expression level is carried out by examining the increase or decrease in expression level according to generation and proliferation of cancer, compared to normal cells. To this end, RT-PCR was performed using total RNAs obtained from cancer cell lines and oligonucleotide of the gene of interest to examine expression levels of the gene in cancer cell lines, compared to normal cells.

Therefore, in the present invention, expression levels of the FLJ25416 gene in colon cancer tissues were analyzed by RT-PCR. RT-PCR of the present invention was carried out using the One-step RT-PCR PreMix kit (iNtRON Biotechnology, Inc., Korea). The kit is manufactured for one time synthesis and amplification of cDNA. RT-PCR was carried out by forming total 20 µl of cocktail consisting of an RNA template (1 µg/reaction) obtained from each cancer cell, specific primers, tertiary distilled water and 8 µl of PreMix (OptiScript™ RT and i-StarTaqTMDNA polymerase). The specific primers used for RT-PCR are listed in Table 1.

Figure 3:
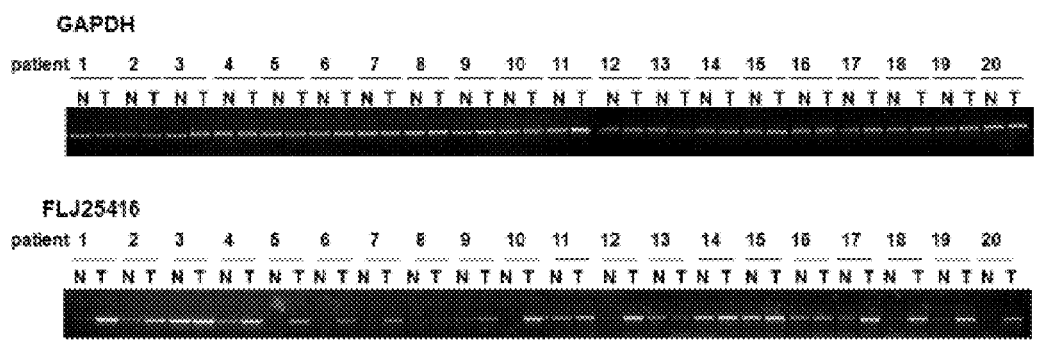
FIG. 3 illustrates comparison of expression levels of FLJ25416 gene in tissues obtained from 20 colon cancer patients, wherein GAPDH is a control.

FIG. 3 shows expression levels of the FLJ25416 gene in cancer patients. In FIG. 3, glyceraldehyde 3-phosphate dehydrogenase (GAPDH) was used as a control for determining a difference in gene expression, N denotes normal, and T denotes tumor. As can be seen from FIG. 3, when comparison was carried out using normal tissues and cancer tissues from 20 patients, mRNA levels of the FLJ25416 gene were increased in cancer tissues from 15 patients, compared to the normal tissues.

This result reveals that an increase in expression levels of the FLJ25416 gene can be used as a diagnostic index for cancer.

EXAMPLE 4

Cloning of FLJ25416 Gene

Vector-cloned gene pBluescript-FLJ25416 was purchased from Korean Unigene Information (KUGI) provided by Korean Bioinformation Center, and amplified by PCR of 37 cycles at 55° C. with a Forward primer including the SalI restriction site (5'-ATTGTCGACAATGAACAGAAGAC-GAAAATTT-3' SEQ ID NO.: 10)), a Reverse primer including the EcoRV restriction site (5'-CCAGATATCTAT-GAAAACAATTCAGGTGA-3' SEQ ID NO.: 11), and the pfu premix (iNtRON, Inc.). The DNA band of the FLJ25416 gene was purified, and then cloned into a pGEM-Teasy vector. DNA sequencing was carried out to identify 2997 bps of the FLJ25416 gene sequence, and cloning was carried out according to the instructions of the manufacturer using the GATE Way system (Invitrogen Corp.,). Before transfection to a pDEST vector, pGEM-Teasy-FLJ25416 pDNA was cleaved with SalI/EcoR5, and then cloned into a pENTR3C vector (Invitrogen Corp.,). LR-reaction between pENTR3C-FLJ25416 and pDEST-EGFP (Invitrogen Corp.,) was carried out to clone EGFP-tagged FLJ25416 gene (EGFP-FLJ25416), and the resulting gene was cloned to pDEST-EGFP (Invitrogen Corp.,) to clone flag-tagged FLJ25416 gene (Flag-FLJ25416). After plasmid pENTR3C-FLJ25416 was mixed with the pDEST-EGFP or pDEST-Flag DNA, an LR clonase II enzyme mixture was added, and then cultured for 1 hour at room temperature. After the culture, proteinase K was added and the resulting mixture was incubated for 10 minutes at 37° C. to terminate the LR reaction. Subsequently, the product was transfected to *E. coli* DH5α competent cells, thereby obtaining a pDEST-EGFP-FLJ25416 and pDEST-Flag-FLJ254156 clones.

EXAMPLE 5

Increase in Cell Growth Rate Due to Overexpression of FLJ25416

5 ml of HEK293T cells (Cell line Bank, Korean Biotechnology Research) were seeded at a concentration of $1.4 \times 10^5$ cells/ml in a 60 mm dish containing Low glucose DMEM medium (GIBCO, 11885) in which a mixture solution (GIBCO, 15140) of 10% bovine calf serum and penicillin (10,000 units/ml)-streptomycin (10 mg/ml) was diluted 100-fold, and then cultured for 24 hours at 37° C. in a 5% $CO_2$ incubator. EGFP-FLJ25416 plasmid DNA was transfected to the cultured cells. After 3 hours and 30 minutes, all medium was removed, the cell pellet was rapidly washed with phosphate buffered saline (PBS) three times, and then 10% serum-containing medium was added. Twenty-four hours after the transfection, the transfected cells were treated with 0.5% EDTA-trypsin to count a cell number using a hemacytometer. After that, the cells were seeded in a 24-well plate at a concentration of $1 \times 10^5$ cells/ml, and then cultured in a 5% $CO_2$ incubator at 37° C. until sulforhodamine B (SRB) assay. Every 12 hours during culture, a cell growth rate for each plate was assessed by SRB assay. For comparison, the cells were transfected with EGFP vector DNA, and treated in the same manner as the HEK293T cells to be used as a control. The result is shown in FIG. 4, in which the horizontal axis denotes time, the vertical axis denotes a cell growth rate, EV denotes a cell transfected into an FLJ25416 gene-absent vector, and O/E denotes a cell transfected into an FLJ25416 gene-cloned vector, resulting in overexpression of FLJ25416.

Figure 4:
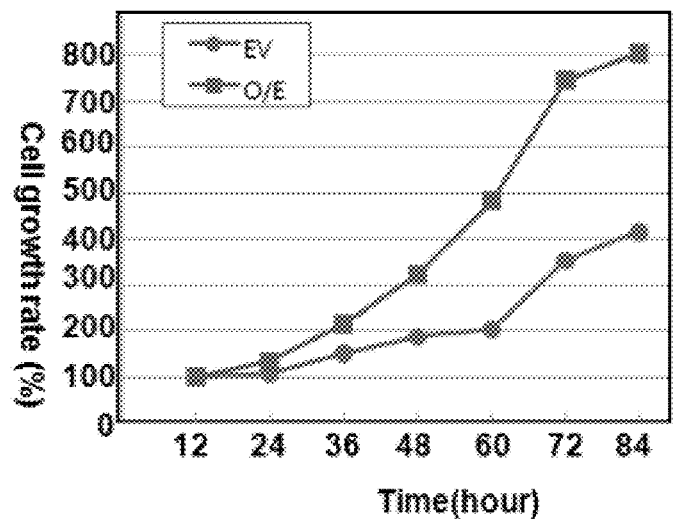
FIG. 4 illustrates a graph showing changes in cell growth rate according to overexpression of the FLJ25416 gene.

As a result, the growth rate of the cell in which the FLJ25416 gene was up-regulated was increased about two-fold, which indicates that the FLJ25416 gene is associated with an increase in cell growth rate that is the characteristic of a tumor cell (FIG. 4). This result reveals that an increase in expression levels of the FLJ24516 gene can be used as a diagnostic index for cancer.

EXAMPLE 6

Growth Inhibition of Cancer Cell Lines by Introduction of siFLJ25416

Changes in cell proliferation rate can be examined by suppressing expression of genes highly expressed in cancer tissues or cancer cell lines through siRNA. Therefore, in the present invention, siRNAs for FLJ25416 were designed to introduce to gastric cancer cell lines Snu638, followed by examining the changes in growth rate of cancer cell lines due to the suppression of mRNA expression of a gene of interest.

First, siRNAs for FLJ25416 and GFP were designed to synthesize (Samchully Pharm. co., Ltd., Korea). The synthetic siRNA was designed based on a base sequence of the gene, which is double-stranded RNA consisting of 19 oligonucleotides with 2 nucleotides 3'-overhangs on either end. The Green fluorescence protein (GFP) was used as a negative control for the siRNA experiment that does not affect cell proliferation.

Figure 5:
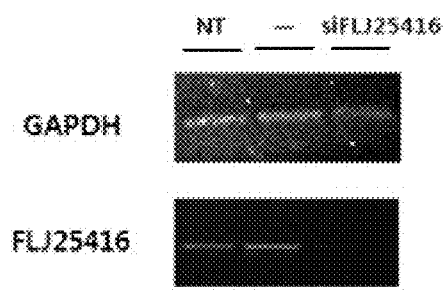
FIG. 5 illustrates photographs showing reduction of mRNA levels and inhibition of cell growth in colon cancer cells after siRNA experiment.
Figure 5:
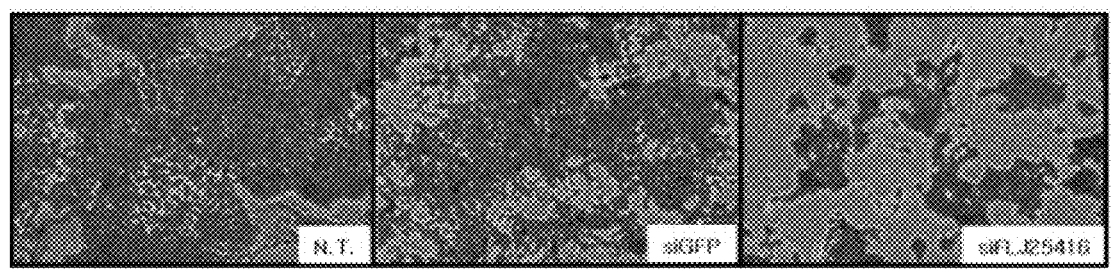

A colon cancer cell line Colo205 (Korean Cell line bank, Seoul National University, Korea) grown in 70% confluency was transfected with siFLJ25416 (sense sequence: SEQ ID NO: 2) and siGFP (sense sequence: SEQ ID NO: 5) using HiPerFect method (Qiagen Co.) for 72 hours. RNA was extracted from each cell, and processed by RT-PCR, thereby confirming a decrease in mRNA level for the gene of interest, and suppression of gene expression due to siRNA (top on FIG. 5). NT denotes a gene expression level in a cell that is not treated with siRNA, and—denotes siGFP of the negative control. siGFP shows that there is no portion targeting to siRNA in a sequence having no homology to the human gene. Each cell was stained with sulfur rhodamine (SRB; Sigma Co.), and a photograph of GFP siRNA-treated cells stained with SRB, which is a control having no great change in cell growth was observed under a microscope. The photograph shows that the growth inhibition occurred in the cells treated siFLJ25416 (bottom on FIG. 5).

Figure 6:
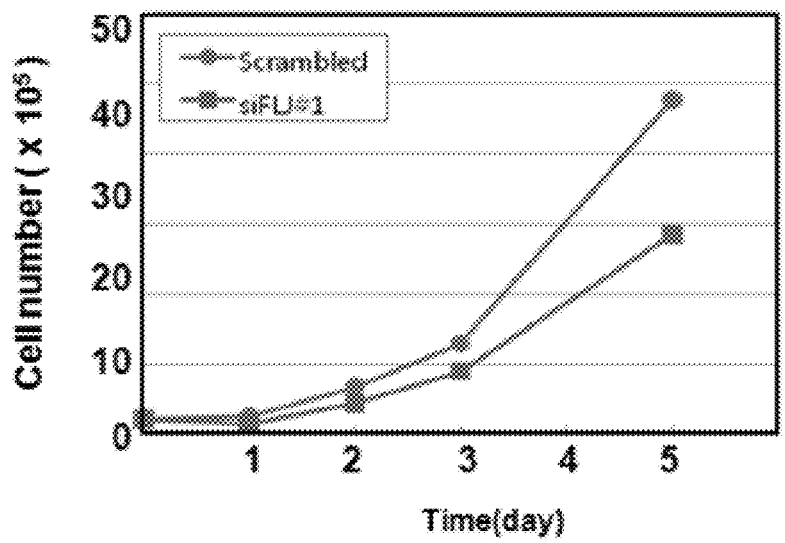
FIG. 6 illustrates a graph showing an inhibitory effect on a cell growth rate in A549 lung cancer cell lines after siRNA experiment.

More specifically, in order to investigate a degree of down-regulation of cell growth by siRNA, 0.5 ml each of A549 cells (Korean cell line Bank, Korea Research Institute of Bioscience and Biotechnology) was seeded in a 24-well plate at a concentration of $1.0 \times 10^5$ cells/ml, and cultured in a 5% $CO_2$ incubator at 37° C. for 24 hours. The cells were transfected with scrambled siRNA (sense sequence: SEQ ID NO: 8) and siFLJ25416 (sense sequence: SEQ ID NO: 2) according to the method described above, and the number of the cells per well was counted by a hemacytometer every 24 hours to compare the cell growth rate. The result is shown in FIG. 6, in which a horizontal axis denotes the date of culture, and a vertical axis denotes a cell number. In addition, siFLJ#1 is a cell line treated with siFLJ25416, and scrambled is a cell line treated with scrambled siRNA. Scrambled siRNA was used as a negative control. As a result, it can be confirmed that the cell line treated with siFLJ25416 significantly decreases in cell growth rate, compared to the cell line treated with scrambled siRNA (FIG. 6).

Figure 7:
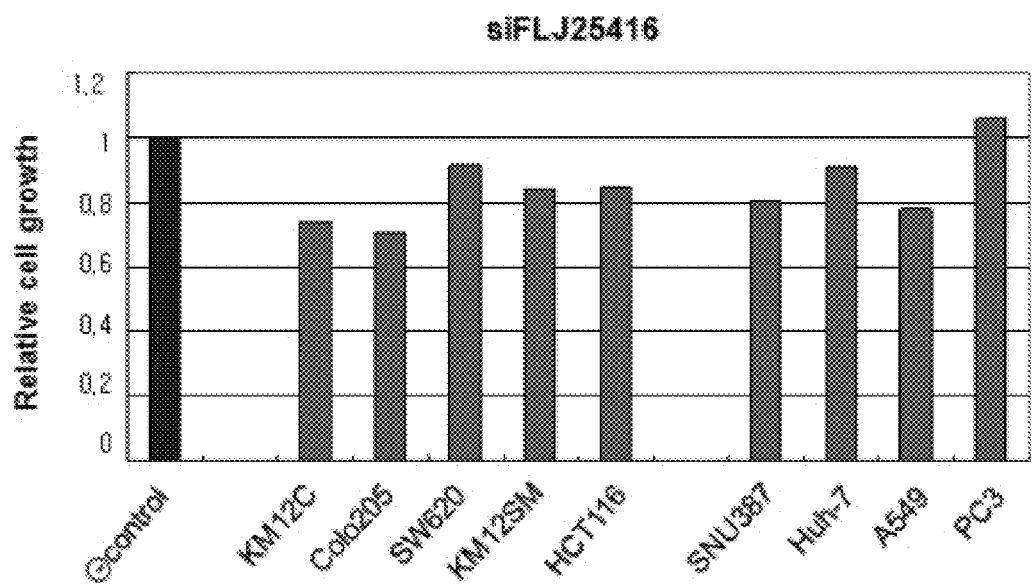
FIG. 7 illustrates a graph showing a degree of cell growth inhibition in colon, lung, liver and prostatic cancer cell lines after siRNA experiment.

In order to examine growth inhibition for cancer cell lines, colon cancer cell lines such as KM12C, KM12SM, Colo205, SW620 and HCT116 (Korean Cell Line Bank, Seoul National University, Korea), a lung cancer cell line such as A549, a liver cancer cell line such as Huh7 (by courtesy of Dr. Dae Ghon Kim, Chonnam National University, Korea), Snu387 (Korean Cell Line Bank, Seoul National University, Korea) and a prostatic cancer cell line such as PC-3 (Korean Cell Line Bank, Seoul National University, Korea) grown to confluencies of 70% were transfected with siFLJ25416 (sense sequence: SEQ ID NO: 2) by the HiPerFect method (Qiagen Co.) for 72 hours for examination of a degree of growth inhibition due to siRNA. The cells were stained with SRB (Sigma Co.) and observed under a microscope. SRB analysis for the cells was carried out, based on GFP siRNA-treated cell lines, which are controls having almost no great change in cell growth to compare the degree of growth inhibition of the cell transfected with the siRNA for the corresponding gene. The result is shown in FIG. 7. Here, a horizontal axis denotes a cell line, and a vertical axis denotes relative cell growth. As a result, in most colon cancer cell lines, the expression inhibition of the FLJ25416 gene results in the cell growth inhibition. As a result, repression of the expression of the FLJ25416 gene induced growth inhibition in most colon cancer cell lines. The results reveal that siRNA for the FLJ25416 gene can cause growth inhibition in colon, lung and liver cancer cell lines, which means that the FLJ25416 gene is capable of being used as a therapeutic target for cancer.

EXAMPLE 7

Construction of shFLJ25416 Adenovirus and Anticancer Effect

1) Construction of sh-FLJ25416 Adenovirus

A shRNA sequence having a loop sequence in-between a complementary sequence to siFLJ25416 (sense sequence: SEQ ID NO: 2) was designed, and a DNA oligonucleotide (SEQ ID NO: 9) coding the shRNA sequence was synthesized to construct a shFLJ25416 fragment. An E1 shuttle vector, pE1sp1A (Ψ) (courtesy of Dr. Chae Ok Yoon, Yeonsei University, Korea), was cleaved with BamHI and HindIII to insert annealed shFLJ25416 fragment, thereby constructing pE1sp1A(Ψ)/shFLJ25416. After that, the aforesaid pE1sp1A (Ψ)/shFLJ25416 was cleaved with BamHI to insert a U6 promoter, and to obtain only the U6 promoter from pE1sp1A (Ψ)/U6shNFE1 (courtesy of Dr. Chae Ok Yoon, Yeonsei University, Korea) having the U6 promoter, restriction with BamHI and electrophoresis were carried out to isolate an about 300-bp DNA fragment. After that, the pE1sp1A(Ψ)/shFLJ25416 was ligased with the U6 promoter, thereby constructing a pE1sp1A(Ψ)/U6/shFLJ25416 shuttle vector. To identify orientation, the shuttle vector was cleaved with EcoRI and HindII, and then an about 400-bp product was indentified by electrophoresis. The constructed pE1sp1A(Ψ)/U6/shFLJ25416 shuttle vector was transfected into BJ5183 E. coli (courtesy of Dr. Chae Ok Yoon, Yeonsei University, Korea) together with a Vdm1d1324 total vector (courtesy of Dr. Chae Ok Yoon, Yeonsei University, Korea) having a modified fiber of adenovirus subtype 5 to induce homologous recombination, thereby constructing a replication-incompetent virus, dlRGD/shFLJ25416. As a control, the same virus having LacZ gene, dlRGD/LacZ (courtesy of Dr. Chae Ok Yoon, Yeonsei University, Korea) was used. All the constructed viruses were proliferated in 293A cells (Invitrogen), purified by CsCl density purification, and then dialyzed. After that, the dialyzed result was lysed using 4% sucrose-contained storage buffer, and then stored in a refrigerator at −80° C. A titer of each virus stock was determined by optical density (O.D) according to absorbance of viral genome using a spectrophotometer.

2) Antitumor Effect by shFLJ25416

Figure 8:
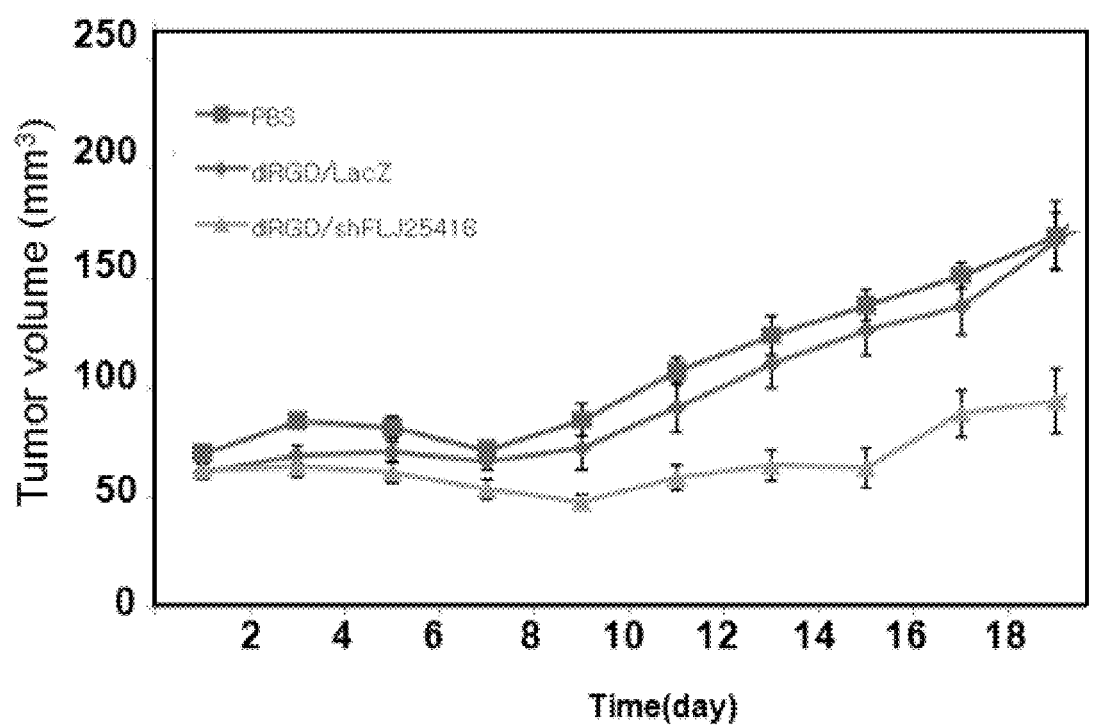
FIG. 8 illustrates a graph showing an anticancer effect of a shRNA-introduced adenovirus on A549 cells.

A human lung cancer cell line A549 used in this experiment was purchased at American Type Culture Collection (ATCC, Manassas, Va., USA). A monolayer of the lung cancer cell line was cultured in DMEM medium containing 10% bovine fetus serum, and then treated with 0.5% trypsin-EDTA (Invitrogen). After that, $7 \times 10^8$ viral cells were suspended in 100 μl of Hanks' Balanced salt solution (HBSS) for subcutaneous injection into abdominal walls of a 7 or 8 week-old nude mouse. About 10 to 14 days after the injection of the tumor cells, when the tumor cells were grown to a size of about 70 to 80 mm³, dlRGD/LacZ adenovirus or dlRGD/shFLJ25416 adenovirus was directly introduced into the tumor cells three times every second day at $5 \times 10^8$ plaque-forming units (PFU) per 50 μl, and then a size of the tumor cell was measured every second day. As a negative control, PBS was used, which was introduced in the same manner as the introduction of the virus. A volume of the tumor was determined by measuring a maximum diameter (a) and a minimum diameter (b) perpendicular to the maximum diameter using a caliper, resulting in a formula of a×b×b'0.523 (Volume of tumor (mm³)=(minimum diameter, mm)²×maximum diameter (mm)×0.523). The result is shown in FIG. 8, in which an x axis denotes time (days), and a y axis denotes tumor volume (mm³). In addition, PBS denotes a PBS-treated negative control, dlRGD/LacZ denotes a dlRGD/LacZ adenovirus-introduced mouse, and dlRGD/shFLJ25416 denotes a dlRGD/shFLJ25416 adenovirus-introduced mouse.

As shown in FIG. 8, in the mouse expressing shRNA by introducing dlRGD/shFLJ25416 adenovirus, an excellent antitumor effect was exhibited. According to FIG. 8, when the tumor size was measured at the 15th day and the 19th day after the introduction, it can be noted that the size of the tumor in the PBS-treated control was significantly increased at the 15th day and the 19th day after the introduction, and the size of the tumor in the dlRGD/LacZ adenovirus-introduced mouse was also increased, similar to the PBS-treated negative control. On the other hand, at the 15th day or the 19th day after the virus introduction, in the dlRGD/shFLJ25416 adenovirus-introduced mouse, tumor growth was inhibited, resulting in a decrease in tumor size, compared to the PBS-treated control, and necrosis of some tumors was observed. As a result, it can be confirmed that the antitumor effect was induced by shFLJ25416 of the present invention.

INDUSTRIAL APPLICABILITY

A composition according to the present invention is effective in diagnosis of cancer, screening of an anticancer drug and cancer treatment. Thus, the present invention will be widely applied to develop a novel biomedicine and a personalized anticancer drug, which has fewer adverse effects, such as a specific therapeutic agent of a cancer target gene. In addition, the present invention can contribute to the development of source technology to prepare the basis for the study of novel cancer-related mechanisms.

What is claimed is:

1. A method of treating colon, lung, or liver cancer expressing an FLJ25416 gene having the sequence of SEQ ID NO: 1 in a subject, said method comprising administering to the subject an effective amount of an siRNA or shRNA inhibitor of the expression of the FLJ25416 gene to inhibit the expression of the gene and thereby inhibit the proliferation of colon, lung, or liver cancer cells in the subject, wherein the siRNA or shRNA inhibitor is sufficiently complementary to SEQ ID NO: 2 to anneal to the mRNA transcript of the gene to result in RNA interference in vivo.

2. The method of claim 1, wherein said siRNA inhibitor comprises the complement of SEQ ID NO: 2.

3. The method of claim 1, wherein said shRNA inhibitor is encoded by SEQ ID NO: 9.

* * * * *